United States Patent [19]

Gough et al.

[11] Patent Number: 5,641,676
[45] Date of Patent: *Jun. 24, 1997

[54] LEUKAEMIA INHIBITORY FACTOR FROM LIVESTOCK SPECIES AND USE THEREOF TO ENHANCE IMPLANTATION AND DEVELOPMENT OF EMBRYONIC CELLS

[75] Inventors: Nicholas Martin Gough; Tracey Ann Willson, both of North Balwyn; Robert Frederick Seamark, Beulah Park, all of Australia

[73] Assignee: Amrad Corporation Limited, Victoria, Australia

[*] Notice: The term of this patent shall not extend beyond the expiration date of Pat. No. 5,418,159.

[21] Appl. No.: 347,688

[22] Filed: Dec. 1, 1994

Related U.S. Application Data

[63] Continuation of Ser. No. 721,529, Aug. 29, 1991, Pat. No. 5,418,159.

[30] Foreign Application Priority Data

Jan. 10, 1989 [AU] Australia .................. PJ2220
Feb. 13, 1989 [AU] Australia .................. PJ2706
Jun. 23, 1989 [AU] Australia .................. PJ4860

[51] Int. Cl.$^6$ .................. C12N 5/00; A61K 49/00; A61D 7/00
[52] U.S. Cl. .................. 435/325; 435/375; 435/377; 435/378; 424/93.7; 600/33; 800/2
[58] Field of Search .................. 435/240.1, 240.3, 435/240.2; 424/93.7; 600/33; 800/2

[56] References Cited

U.S. PATENT DOCUMENTS 5,418,159  5/1995  Gough et al. .

FOREIGN PATENT DOCUMENTS

US88/04700  8/1989  WIPO .

OTHER PUBLICATIONS

Gearing et al. (1987) "Molecular Cloning and Expression of cDNA Encoding a Murine Myeloid Luekaemia Inhibitory Factor (LIF)" *EMBO J.* 6, 3995–4002.

Smith et al. (1988) "Inhibition of Pluripotential Embryonic Stem Cell Differentiation by Purified Polypeptides" *Nature* 336, 688–690.

Williams et al. (1988) "Myeloid Leukaemia Inhibitory Factor Maintains the Developmental Potential of Embryonic Stem Cells" *Nature* 366, 684–687.

Robertson et al. (1990) "In Vitro Models of the Maternal–Fetal Interface" in Molecular and Cellular Immunology of the Maternal–Fetal Interface, Wegmenn, et al., eds., Oxford University Press, New york, 191–206.

Gearing et al (1987) EMBO J. 6, 3995–4002.

*Primary Examiner*—Jasemine C. Chambers
*Assistant Examiner*—Deborah Crouch
*Attorney, Agent, or Firm*—Scully, Scott, Murphy & Presser

[57] ABSTRACT

Disclosed is the in vitro development of mammalian embryos to the implantation stage by culturing the embryos in a medium containing leukemia inhibitory factor (LIF).

7 Claims, 12 Drawing Sheets

```
GATCCCCACAGAGCTG--GGACAGGAAGTTTTGA
AGTGAGCGGCCACAGTGGGGGAAGGAGAAACACA
CTTGGGAGATGAGGGTGAGCAGAACCCCTCCCC
ATCCTGGGAGGTGGGGAGATAGGGTCAGCTCTTC
CCTGGACCAGCTTCCTACTGGTACAAATAGCTC
AGGTGGTGACATCGTCAGGGCTGGGGAAGAGAGA

CCTTGCCTACCCTTTCACCTCCCTAATCATGGCT
    SerProLeuSerIleThrProValAsnAlaThrC
AGCCCCCTTTCCATCACTCCTGTCAATGCCACCT
 snSerSerAlaAsnAlaLeuPheIleLeuTyr
ACAGCAGTGCCAACGCCCTCTTTATTCTCTACGT
TGCTGTGGGACCTGGGCTGGCGGGCTGGCTAGGG
CCTGGCCAAGGCTCGGTCACTTTCCCCGGGGGCC
CACCTCTGGAGCAAGAGGCACATGAGAGGAGAGA
. . . . . . . . . . . . . . . . . . . . . . . . . . .
GTCCAAGCTGCCTTGGGGCAATTGAGTGGGTCA

GGGAAGCCCTGTCCCTGACTCCATGTCACCTCCC
 CysGlyProAsnValThrAsnPheProProPheH
TGTGGCCCCAACGTGACCAACTTCCCGCCCTTCC
 erLeuGlyAsnIleThrArgAspGlnArgSerLe
CCCTGGGCAACATCACGCGGGACCAAAGGAGCCT
 uSerAsnValLeuCysArgLeuCysAsnLysTyr
CAGCAATGTGCTCTGCCGCCTGTGCAACAAGTAC
 LysLeuGlyCysGlnLeuLeuGlyLysTyrLysG
AAGCTGGGCTGTCAGCTCCTGGGGAAGTATAAGC
TTAGACTTAGGTGACTCTCAAACTGTGCCGGGGC
CTGTCTCCTCTCCTCAGGGGTGGGCTGTGATGAA
CCAGGCATTGGTGTTGGGCTGCCCCCTCCACCAT
```

*Fig.2a.*

```
GGGATT-TTTGGTCAAGGAGAGGGGAATTGCAGA
GAGAAGATGGGCAAAGGAGATGGAATTAGGGGAC
CCTTCCCCATGGTCCAGCTCGCTCTGGGAGACT
TCTCTGTGACCTGCTGGGCTTGGGGTGTGGTGCC
CTTTCCTGCCCCTTGCTACCAGAGGTAGAGAGTT
GCTGGAGGCTGAGAGGGGACACTGGTGTCCCTAA
                GlyValValProLeuL
CGTTTTGCCTGTTTGCAGGAGTTGTGCCCTGC
ysAlaThrArgHisProCysHisSerAsnLeuMe
GTGCCACACGTCACCCATGTCACAGCAACCTCAT

AAGTTCACCCCCCTTGCCCGACCCCAGGGTGCTG
AAGGGAAGGGAGGGGGGCTCGGTCCTACCATGTG
CTGTTACATATTGGCAGAGCTGCCTGGAGGCGGG
AGGAGG........................
......GATCCTCCGCACGGCCCGGGTGTGCGTT
TCGTGCCAGTTTGGGGGCAGTGGGGACCTGAGGC
                  TyrThrAlaGlnG
CTCTGTGCCTCTGCCCCTCAGTACACAGCCCAGG
isAlaAsnGlyThrGluLysAlaArgLeuValGl
ACGCCAACGGCACCGAGAAGGCCCGGCTGGTGGA
uAsnProGlyAlaValAsnLeuHisSerLysLeu
CAATCCTGGTGCTGTGAACCTGCACTCCAAGCTG
HisValAlaHisValAspValAlaTyrGlyProA
CACGTGGCCCATGTGGATGTGGCCTACGGCCCCG
lnValIleSerValLeuAlaArgAlaPhe***
AGGTCATCTCTGTGCTAGCCCGGGCCTTCTGATG
CCAGAACATCACCAGACCCAAGTGGGGGTTGCTG
GCAGAACCCAAACTCCCGGAGGCAGAACCAACTA
CACCACCTTGTTCCCTCAGTCAGAGTCTTCATGA
```

*Fig. 2b.*

```
ATTGGGGTGGAGTTGAGGGTCCTAGATAGGGG        100
GAATGGTCAGTGAGCCAAAATCATGTGCTAGG        200
CAGGTATGAAGTAACACTTAAGAATTTGGACC        300
CTCCAGCCAAAGGCCAGGATGGTTGTTGTCAC        400
AGCCATCTGGAGAGAGGGAGATAGAGGAGGAG        500
AGGAGACGAGGCGCATCCTATCCTGGGAGCCC        600
euLeuValLeuHisTrpLysHisGlyAlaGly
TGCTGGTTCTGCACTGGAAACACGGGGCAGGG        700
tAsnGlnIleLysAsnGlnLeuAlaHisValA
GAACCAGATCAAGAACCAGCTGGCGCACGTCA        800

AGGAAGGAAGGAGGGAGGGAGGGGCTGGGGTT        900
CAGAGTCCCACAGCTTCCGCCCCACTCCCCAC       1000
GAGGCCTGACACTTCGAGCCTCAGGCTTCCTC       1100
.... ‾ 0.2 kbp ..................
CACACCCACAGTTACTTCTGGTTCTCAGGACG       1200
CAAGACCTGACCCAGAGGCTTGGAGGCAGCGC       1300
lyGluProPheProAsnAsnLeuAspLysLeu
GGGAGCCATTTCCAACAACTTGGACAAGCTG        1400
uLeuTyrArgIleIleAlaTyrLeuGlyAlaS
GCTGTACCGCATCATCGCCTACCTTGGCGCCT       1500
AsnAlaThrAlaAspSerMetArgGlyLeuLe
AACGCCACGGCGGACAGCATGCGAGGCCTCCT       1600
spThrSerGlyLysAspValPheGlnLysLys
ACACCTCGGGCAAGGACGTCTTCCAGAAGAAG       1700

GAAGGTCCCCTAGCACCCCGTGACCTGAGGTC       1800
ACAGACCCGGGAGGGAGGGGGG---TTCTTAG       1900
GAGAAGGCATCCCTTGTTCTGGGAGACTGCAG       2000
TC                                    2070
```

*Fig. 2c.*

```
GATCCCGGCTAAATATAGCTGTTTCTCTGTCTTA

GGCATCTGAGGTCTCGTCCAAGGTCCTCTGGAGC
. . . . . . . . . . . . . . . . . . . . . . . . . . . . . . .
CTGCCCAGGGAAGACAGAGGGGGGTCAGGGAGTC
         GlyValValProLeuLeuLeuVa
GCCTCTCCCCAGGAGTCGTGCCCCTGCTGCTGGT
rHisHisProCysProSerAsnLeuMetSerGln
ACACCACCCATGCCCAGCAACCTCATGAGCCAG
CCCCAGGGGACAAGAAGGGAGGGAGGGCCCGGG
TGTCTCGGGGAGGGGGGGGGAGTGTTGGGGGGGAC
AGGCAAGACACCACATTTTCCTTTCTGTCCCCGT
. . . . . . . . . . . . . . . . . . . . . . . . . . . . . .
GGCGTTGGGTCCTCGTGCTATGGGTGGGCACACT

TCCTGGGGTCACCTACCTTCCGTCCCTCTACTCC
rAspPheProProPheGlnProAsnGlyThrGlu
GGACTTCCCGCCCTTCCAGCCCAACGGCACGGAG
ArgAspGlnLysThrLeuAsnProThrAlaHisS
CGGGACCAGAAGACCCTCAACCCCACGGCGCACA
rgLeuCysSerLysTyrHisValAlaHisValAs
GCCTGTGCAGCAAGTACCACGTGGCCCACGTGGA
uLeuGlyLysTyrLysGlnValMetAlaValLeu
GCTGGGAAAATACAAGCAGGTCATGGCCGTGTTG
```

*Fig.3a.*

```
CAACACAGGCTCCAGTATATAAATCCGGCAAA
               MetLysIleLeuAlaAla
ACACAGCCATGATGAAGATCTTGGCGGCAGG
 ~1.5 kbp  . . . . . . . . . . . . . . . . . .
CCTCCACTGGCATCCAGTGTGACCCCCAAGC
 LeuHisTrpLysProGlyAlaGlySerProL
CTTGCACTGGAAACCCGGGGCGGGGAGCCCC
 IleArgSerGlnLeuAlaGlnLeuAsnGlyTh
ATCAGGAGCCAGCTGGCACAGCTCAATGGCAC
AGGAGGGGCGAGGAACAGAAACCAGGCAGCAG
GCCCAGGAAGAAGGTGAGGGCAGTGGGTGAAA
GTCGTCCTC. . . . . . . . . . . . . . . . . .
. . . . . . . . . . TCGCACCTACCACGCTGCTGCTG
GAGCACCCTCCAGCTCCTGCCCCAGGAGCTGG
   TyrThrAlaGlnGlyGluProPheProA
TCAGTACACAGCCCAAGGGGAGCCGTTCCCCA
 LysValArgLeuValGluLeuTyrArgIleVa
AAGGTCAGGCTGGTGGAGCTGTACCGCATCGT
 erLeuHisSerLysLeuAsnAlaThrAlaAsp
GCCTGCACAGCAAACTCAACGCCACGGCGGAC
 pValAlaTyrGlyProAspThrSerGlyLysA
CGTGGCCTATGGCCCGGACACCTCGGGCAAGG
 AlaGlnAlaPhe***
GCGCAGGCCTTCTAGGTGGCCGGCCGTGAACT
```

*Fig.3b.*

```
TTCCCCATTTGAGCATGAACCTCTGAAAACGGCC

TAAAT..........................
.....AGATGCTGAGACAAAGTGAAAACCCACC
ACCCGTCCACCTCTGCGCTCACGGCTCCTCCCT
 euProIleAsnProValAsnAlaThrCysAsnTh
TTCCATCAACCCCGTCAACGCCACCTGCAACAC
 rAlaAsnAlaLeuPheIleLeuTyr
TGCCAACGCCCTCTTTATTCTCTATGTAAGTTAA
GCAGACAGGAAGGTGCTGCCGAGAGGGCTGTGGG
GTGCAAGTGTGTGGTGCGCCGCCGAGGGCAGAC
0.2kbp  .........................
GTTCCACGCCAGTTCTAGCTGTCTCCAGGGCAA
CTGGAGGCAGGGCCGGAACACTGCCCCCCTGAC
 snAsnLeuAspLysLeuCysGlyProAsnValTh
ACAACCTGGACAAGCTGTGCGGCCCCAATGTGAC
 lAlaTyrLeuGlyThrAlaLeuGlyAsnIleThr
GGCCTACCTTGGCACCGCCCTGGGCAACATCACC
 ThrLeuArgGlyLeuLeuSerAsnValLeuCysA
ACGCTGCGGGGCCTGCTTAGCAACGTGCTGTGCC
 spValPheGlnLysLysLysLeuGlyCysGlnLe
ACGTCTTCCAGAAGAAGAAGCTGGGGTGTCAGCT

GATGGGTCCCAGGAGGGGATCC
```

```
+1
GlyAlaGlySerProLeuProIleThrProValAsnAlaThrCysAlaIleArgHisPro*
GlyAlaGlySerProLeuProIleThrProValAsnAlaThrCysAlaIleArgHisPro*
GlyAlaGlySerProLeuProIleAsnProValAsnAlaThrCysAsnThrHisHisPro*
GlyAlaGlySerProLeuSerIleThrProValAsnAlaThrCysAlaThrArgHisPro

AsnAlaLeuPheIleSerTyrTyrThrAlaGlnGlyGluProPheProAsnAsnValGlu
AsnAlaLeuPheIleLeuTyrTyrThrAlaGlnGlyGluProPheProAsnAsnLeuAsp
AsnAlaLeuPheIleLeuTyrTyrThrAlaGlnGlyGluProPheProAsnAsnLeuAsp
AsnAlaLeuPheIleLeuTyrTyrThrAlaGlnGlyGluProPheProAsnAsnLeuAsp

ThrLysLeuValGluLeuTyrArgMetValAlaTyrLeuSerAlaSerLeuThrAsnIle
AlaLysLeuValGluLeuTyrArgIleValAlaValValTyrLeuThrSerLeuGlyAsnIle
ValArgLeuValGluLeuTyrArgIleValAlaIleValAlaTyrLeuThrAlaLeuGlyAsnIle
AlaArgLeuValGluLeuTyrArgIleIleAlaIleAlaTyrLeuGlyAlaSerLeuGlyAsnIle
```

Fig. 4b.

```
M: ThrArgAspGlnLysValLeuAsnProThrAlaValSerLeuGlnValLysLeuAsnAla
H: ThrArgAspGlnLysValIleLeuAsnProSerAlaLeuSerLeuHisSerLysLeuAsnAla
O: ThrArgAspGlnLysThrLeuAsnProThrAlaHisSerLeuHisSerLysLeuAsnAla
P: ThrArgAspGlnArgSerLeuAsnProGlyAlaValAsnLeuHisSerLysLeuAsnAla

M: ArgValGlyHisValAspValProProValProAspHisSerAspLysGluAlaPheGln
H: HisValGlyHisValAspValThrTyrGlyProAspThrSerGlyLysAspValPheGln
O: HisValAlaHisValAspValAlaTyrGlyProAspThrSerGlyLysAspValPheGln
P: HisValAlaHisValAspValAlaTyrGlyProAspThrSerGlyLysAspValPheGln

M: GlnAlaPhe
H: GlnAlaPhe
O: GlnAlaPhe
P: ArgAlaPhe
```

LEUKAEMIA INHIBITORY FACTOR FROM LIVESTOCK SPECIES AND USE THEREOF TO ENHANCE IMPLANTATION AND DEVELOPMENT OF EMBRYONIC CELLS

This is a continuation of application Ser. No. 07/721,529 now U.S. Pat. No. 5,418,159 issued May 23, 1995 filed on Aug. 29, 1991 corresponding to: International Application PCT/AU90/00001, filed on Jan. 9, 1990 and which designated the U.S.

The present invention relates generally to leukaemia inhibitory factor (LIF) from livestock species. More particularly, the present invention relates to the identification, cloning and structural characterisation of genes encoding LIF from livestock species. The present invention also relates to the use of LIF from livestock species in the enhancement of development of mammalian embryos and in maintaining ES cell lines in vitro.

LIF is a protein that has previously been cloned, produced and purified, in large quantities in purified recombinant form from both *E.coli* and yeast cells (International Patent Application No. PCT/AU88/00093.) LIF has been defined as a factor, the properties of which include:

1. the ability to suppress the proliferation of myeloid leukaemic cells such as M1 cells, with associated differentiation of the leukaemic cells; and
2. the ability to compete with a molecule having the defined sequence of murine LIF or human LIF (defined in International Patent Application No. PCT/AU88/00093) for binding to specific cellular receptors on M1 cells or murine or human macrophages. In addition to the biological properties previously disclosed for murine and human LIF, LIF has been found to have the following additional properties:
   (a) it maintains in vitro in the absence of feeder cells, the pluripotential phenotype of murine embryonic stem (ES) cell lines: D3 and EK-cs4 (derived from strain 129/SV blastocysts) and CBL63 and HD5 (derived from C57BL/6 blastocysts) as disclosed in International Application No. PCT/AU89/00330;
   (b) it allows the aforementioned ES cell lines, after passage in vitro in the presence of LIF, to contribute to the tissues of chimaeric mice when re-introduced into the embryonic environment;
   (c) it demonstrates selective binding to high affinity receptors on murine ES (EK-cs1 and D3) and embryonic carcinoma (EC) (PCC3-3A, F9, PC13, P19 and MG2) cells; and
   (d) specific binding of $^{125}$I-LIF to high affinity receptors is not in competition with insulin, IGF-I, IGF-II, acidic and basic FGF, TGFβ, TNFα, TNFβ, NGF, PDGF, EGF, IL-1, IL-2, IL-4, GM-CSF, G-CSF, Multi-CSF nor erythropoietin, but is in competition with murine and human LIF.

Accordingly, LIF is a potent hormone having utility in the general area of in vitro embryology, such as in maintaining ES cell lines and increasing the efficiency of embryo transfer and thus has important applications in the livestock industry. This is particularly apparent in the use of ES cells to provide a route for the generation of transgenic animals.

A major difficulty associated with present in vitro fertilisation (IVF) and embryo transfer (ET) programmes, particularly in humans, is the low success rate "achieved" on implantation of fertilised embryos. Currently, in human IVF programmes, the implantation rate may be as low as 10%, leading to the present practice of using up to four fertilised embryos in each treatment which, in turn, leads occasionally to multiple births. Accordingly, there is a need to improve the implantation rate in human IVF programmes. Similarly, in IVF and ET treatments in domestic animals such as sheep, cattle, pigs and goats, it is highly desirable for economic reasons to have as high an implantation rate as possible so as to reduce the numbers of fertilised embryos lost and unsuccessful treatment procedures performed.

In the development of a mammalian embryo, the fertilised egg passes through a number of stages including the morula and the blastocysts stages. In the blastocyst stage, the cells form an outer cell layer known as the trophectoderm (which is the precursor of the placenta) as well as an inner cells mass (from which the whole of the embryo proper is derived). The blastocyst is surrounded by the zona pellucida, which is subsequently lost when the blastocyst "hatches". The cells of the trophectoderm are then able to come into close contact with the wall of the uterus in the implantation stage. Prior to formation of the embryo proper by the inner cell mass by gastrulation, the whole cell mass may be referred to as "pre-embryo".

Although LIF from one species may be effective, for example in maintaining ES cell lines from a different or heterologous species, it may be preferable to develop homologous systems employing LIF and ES cell lines derived from the same species. It has now been found, in accordance with the present invention, that murine LIF DNA can be used to identify the LIF gene from a wide range of mammalian genomes and to clone the gene encoding LIF from livestock species such as pigs and sheep and hence, provide a source of LIF for use in the development of a variety of in vitro embryogenic procedures, such as ES cell lines and embryo transfer in livestock species.

Furthermore, it has also been found that when LIF is included in an in vitro embryo culture medium, the hatching process is enhanced leading to an increased number of embryos completing the development stage by undergoing developmental changes associated with implantation. As a result, the implantation rate for IVF and ET programmes can be significantly improved by the use of LIF in the in vitro embryo culture medium.

Accordingly, one aspect of the present invention relates to the LIF gene from any livestock species which can be detected by cross-hybridization with a nucleotide probe to murine LIF. That is, a first nucleic acid molecule, encoding a livestock species leukaemia inhibitory factor, comprising a nucleotide sequence capable of hybridizing to a second nucleic acid molecule which encodes murine leukaemia inhibitory factor or part thereof.

A "nucleotide probe" as used herein means a DNA or RNA sequence or any combination thereof capable of detecting complementary sequences by hybridization techniques such as, but not limited to, Southern or Northern blotting or colony hybridization. The probe may comprise a small number of nucleotides (eg. 6–20) or may be the entire gene or part or parts of a gene. The probe may be labelled with a detectable signal (eg. radioactive isotope).

By "nucleic acid" is meant a polymer of four or more nucleotides in which the 3' position of one nucleotide sugar is linked to the 5' position of the next nucleotide by a phosphodiester bridge. The nucleic acid contemplated herein may be linear or circular, single or double stranded DNA or RNA.

"Livestock species" is used herein in its most general sense encompassing, but not limited to, sheep, cows, pigs, horses, donkeys and the like. Even more preferably, the livestock species is sheep or pig.

By "hybridizing" is meant the ability to form a double stranded third nucleic acid by the formation of base pairs between single strands of the first and second nucleic acid under appropriate conditions of stringency. The stringency conditions employed will depend on the relative homology between the relevant strands of the first and second nucleic acid molecules. Convenient conditions for stringency can be found in Maniatis et al. (1982) or by reference to the non-limiting examples of the present specification.

Accordingly, where the nucleic acids are double stranded molecules, the present invention relates to a first nucleic acid encoding part or parts of livestock species leukaemia inhibitory factor comprising on one strand thereof a nucleotide sequence capable of being hybridized to by a strand of a second nucleic acid encoding part or parts of murine LIF.

Although the present invention is exemplified by the second nucleic acid encoding murine LIF or parts thereof, it is possible that a different nucleic acid encoding non-murine LIF but which is capable of hybridizing to murine-LIF nucleic acid could be used. The use of non-murine LIF-encoding second nucleic acid is, therefore, still encompassed by the present invention provided said non-murine LIF-encoding nucleic acid is capable of being hybridized to by the said second nucleic acid encoding murine LIF or parts thereof.

The present invention extends to nucleic acids encoding full length LIF molecules or to part or parts of LIF molecules. Accordingly, the nucleic acids may represent the full coding sequence of mammalian LIF or carry single or multiple nucleotide additions, deletions and/or substitutions or may represent just a portion of the LIF molecule, for example an N-terminal or C-terminal portion. Accordingly, "parts" of a LIF molecule includes any one or more contiguous series of amino acids contained within a LIF molecule and further includes natural, chemical and/or recombinant derivatives.

Another aspect of the present invention relates to a recombinant DNA molecule containing the nucleotide sequence encoding LIF from a livestock species or substantially similar analogues thereof, either completely or in part, in a form in which said nucleotide sequence is able to direct the synthesis and production of said LIF, either completely or in part. This aspect of the invention also extends to cloning vectors such as plasmids and expression vectors and host cells having such recombinant DNA molecules inserted therein. Furthermore, the invention also extends to synthetic livestock LIF, either complete or in part, or substantially similar analogues thereof, produced by expression of such recombinant DNA molecules.

Accordingly, this aspect of the present invention relates to recombinant DNA or RNA molecules comprising the first nucleic acid defined above operably linked to one or more regulatory regions such that in the appropriate host and under the requisite conditions, the first nucleic acid will be transcribed and translated into a recombinant LIF product or derivative or part thereof. The recombinant molecule will further comprise a replication region appropriate for the intended host or may comprise more than one replication region if more than one host is used. Vectors and suitable hosts are known to those skilled in the art and are discussed in the non-limited examples herein, in PCT/AU88/00093 and in Maniatis et al. (1982).

The present invention, therefore, extends to recombinant livestock LIF, and preferably, but not limited to, ovine and porcine LIF or derivatives or parts thereof. Such derivatives or parts thereof are discussed above but include single or multiple amino acid substitutions, deletions and/or additions to or in the natural or synthetic livestock LIF molecule. Conditions for preparing recombinant LIF are disclosed in PCT/AU88/00093 although variations and/or modifications to these conditions may vary depending on the host cell used. Any such variations and/or modifications are within the scope of the subject invention. The host cells may be eukaryotic (eg yeast, mammalian, plant etc.) cells or prokaryotic (eg *Escherichia coli*, Bacillus sp, Pseudomonas sp etc.).

Yet another aspect of the present invention provides a source of recombinant livestock LIF for use in in vitro embryology. Accordingly, the present invention contemplates a method for maintaining ES cell lines in in vitro culture while retaining a pluripotential phenotype which method comprises contacting said ES cell lines with an ES cell line maintaining effective amount of livestock species LIF for sufficient time and under appropriate conditions.

Still yet another aspect of the present invention relates to a method for enhancing the in vitro development of a mammalian embryo to the implantation stage, which method comprises the step of culturing the embryo in vitro in a culture medium containing an effective amount of mammalian LIF.

Preferably, pre-embryos are allowed to develop to the stage of formation of the blastocyst (post-hatching embryos) before LIF is included in the culture medium as LIF has been found to enhance the hatching process leading to an increased number of embryos completing the developmental stage. As is demonstrated below, however, the inclusion of LIF in the culture medium prior to the formation of the blastocyst, or both prior to and following blastocyst formation, also increases the number of pre-embryos completing the developmental stage by undergoing development changes associated with implantation. As a result, the implantation rate for IVF and ET programmes can be significantly improved by use of LIF in the in vitro culture medium.

"Mammalian embryos" is used in its broadest sense encompassing human, ruminant and other livestock animals. It will be appreciated that while the subject invention is exemplified herein by the development of murine embryos in vitro, the present invention extends to the use of LIF in the development of embryos of other species including humans, ruminants and animals such as sheep, cattle, horses, donkeys, goats and the like.

The present invention, also extends to a method for in vitro fertilisation and subsequent implantation of a mammalian embryo which is characterised in that the embryo is cultured in vitro in a culture medium containing an effective amount of mammalian LIF prior to implantation.

"Mammalian LIF" encompasses human, murine, ruminant and other or livestock LIF such as from sheep, pigs, cows, goats, donkeys and horses and the like.

In the figures:

FIGS. 2a–2c shows the nucleotide sequence of the porcine LIF gene. The mRNA-synonymous strand of 2 portions of the porcine LIF gene Mounting to 2.07 kbp of sequence derived from clone λPGLIF-E2, spanning the two exons encoding the mature protein of the porcine LIF gene are listed 5' to 3' using the single letter code according to standard practice, where A refers to deoxyadenosine-5'-phosphate, C refers to deoxycytidine-5'-phosphate, G refers to deoxyguanosine-5'-phosphate and T refers to deoxythyjidine-5'-phosphate. The amino acid sequence encoded by the two exons of the porcine LIF gene defined by homology with the murine, human and ovine cDNA and gene sequences (International Application No. PCT/AU88/00093) is listed above the gene sequence, where ALA is Alanine, ARG is Arginine, Asn is Asparagine, ASP is Aspartic acid, CYC is Cystein, GLN is Glutamine, GLU is Glutamic acid, GLY is Glycine, HIS is Histidine, ILE is Isoleucine, PHE is Phenylalanine, PRO is proline, SER is Serine, THR is Threonine, TRP is Tryptophan, TYR is Tyrosine, and VAL is Valine.

FIGS. 3a–3c shows the nucleotide sequence of the ovine LIF gene. The mRNA-synonymous strand of three portions of the ovine LIF gene amounting to ~1.5 kbp of sequence derived from clone λOGLIFR2, spanning the three protein coding regions of the ovine LIF gene are listed 5' to 3' using the single letter code according to standard practice, where A refers to deoxyadenosine-5'-phosphate, C refers to deoxycytidine-5'-phosphate, G refers to deoxyguanosine-5'-phosphate and T refers to deoxythymidine-5'-phosphate. The amino acid sequence encoded by the three exons of the ovine LIF gene defined by homology with the murine and human cDNA and gene sequences (International Application No. PCT/AU88/00093) is listed above the gene sequence, where ALA is Alanine, ARG is Arginine, ASN is Asparagine, ASP is Aspartic acid, CYS is Cysteine, GLN is Clutamine, GLU is Glutamic acid, GLY is Glycine, HIS is Histidine, ILE is Isoleucine, PHE is Phenylalanine, PRO is Proline, SER is Serine, THR is Threonine, TRP is Tryptophan, TYR is Tyrosine, and VAL is Valine.

EXAMPLE 1

Figure 1:
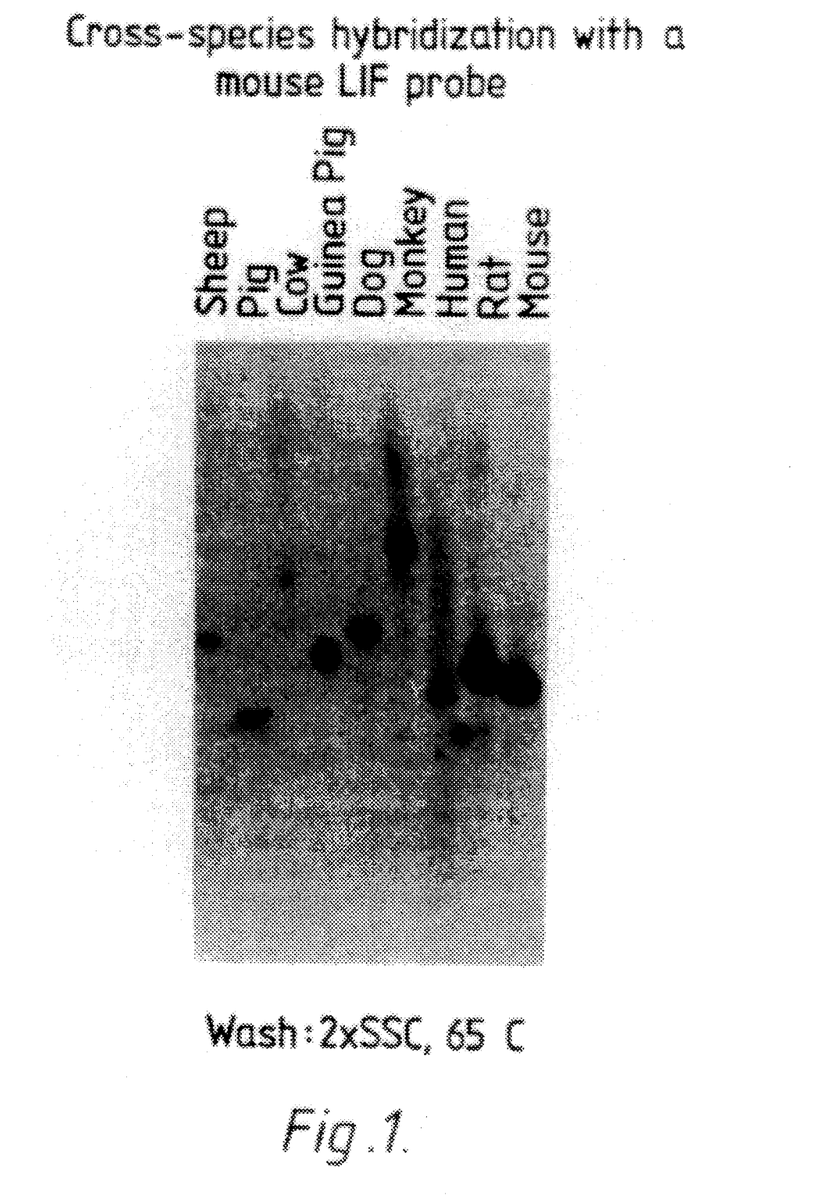
FIG. 1 relates to Example 1. The identification of LIF gene homologues in DNA from a variety of mammalian species by cross-hybridization with a murine cDNA probe.
Figure 2:
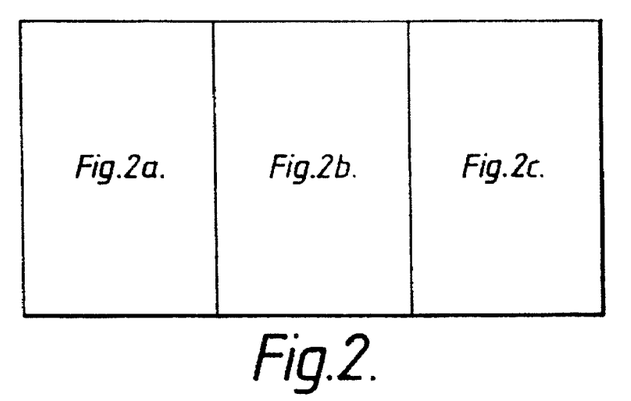
Figure 2A:
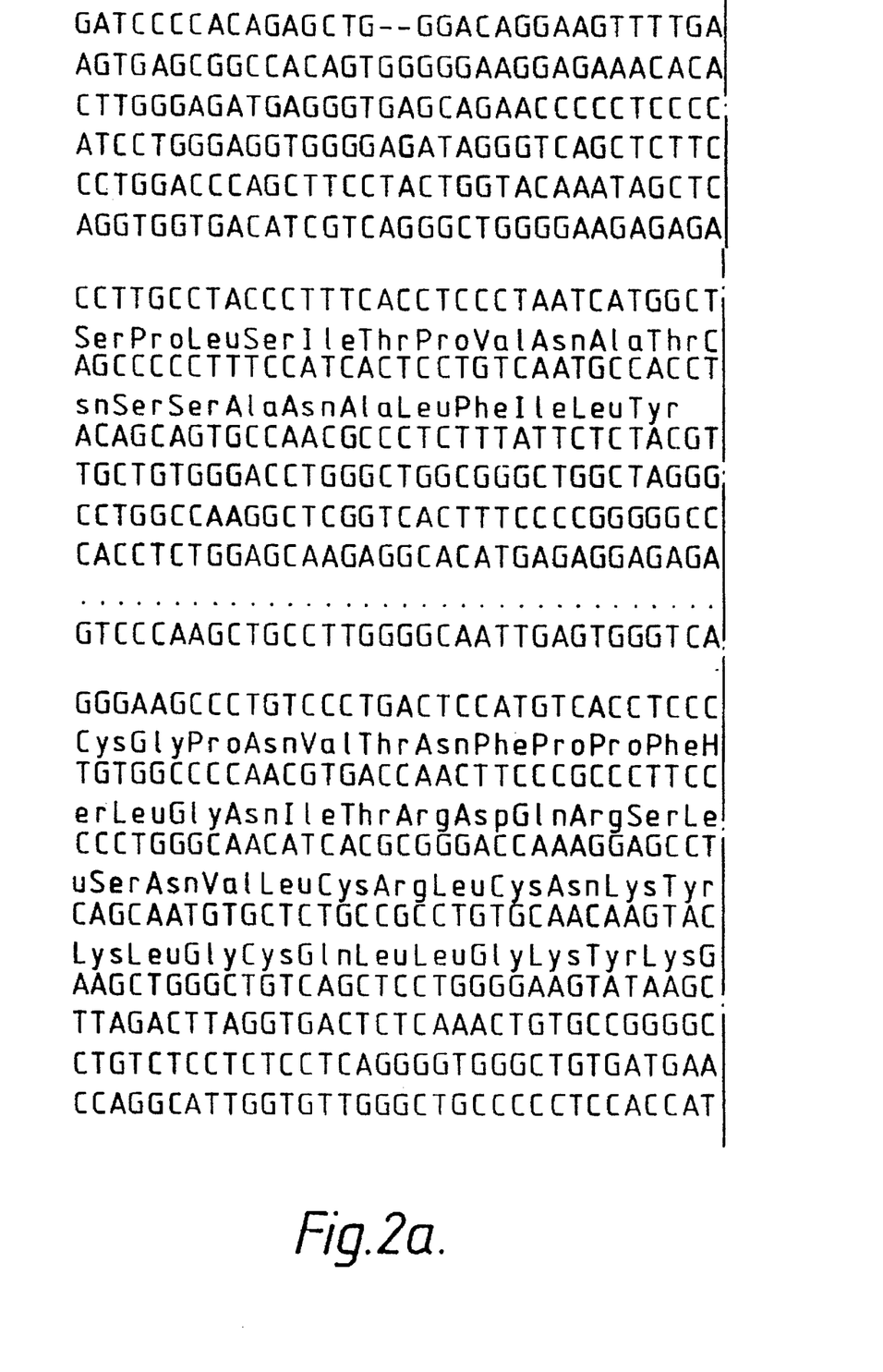
Figure 2B:
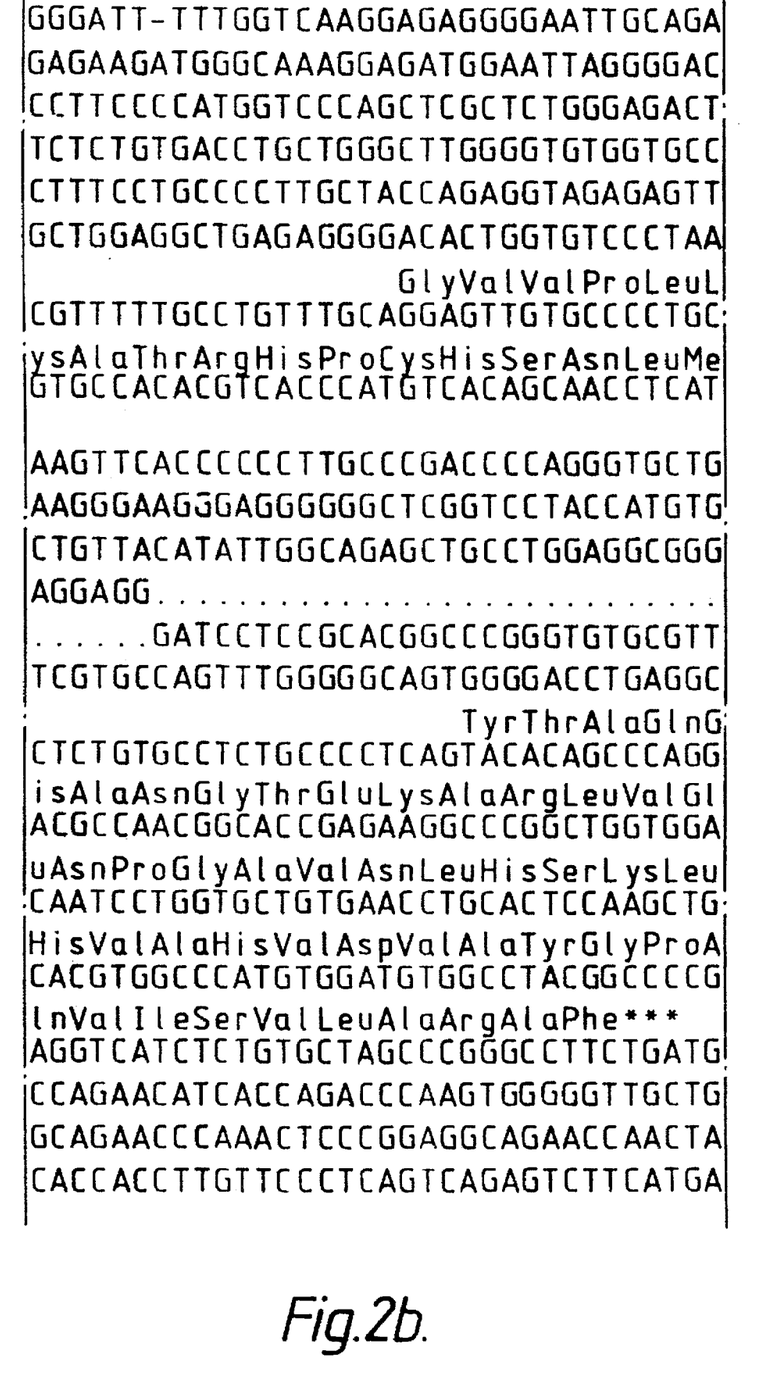
Figure 2C:
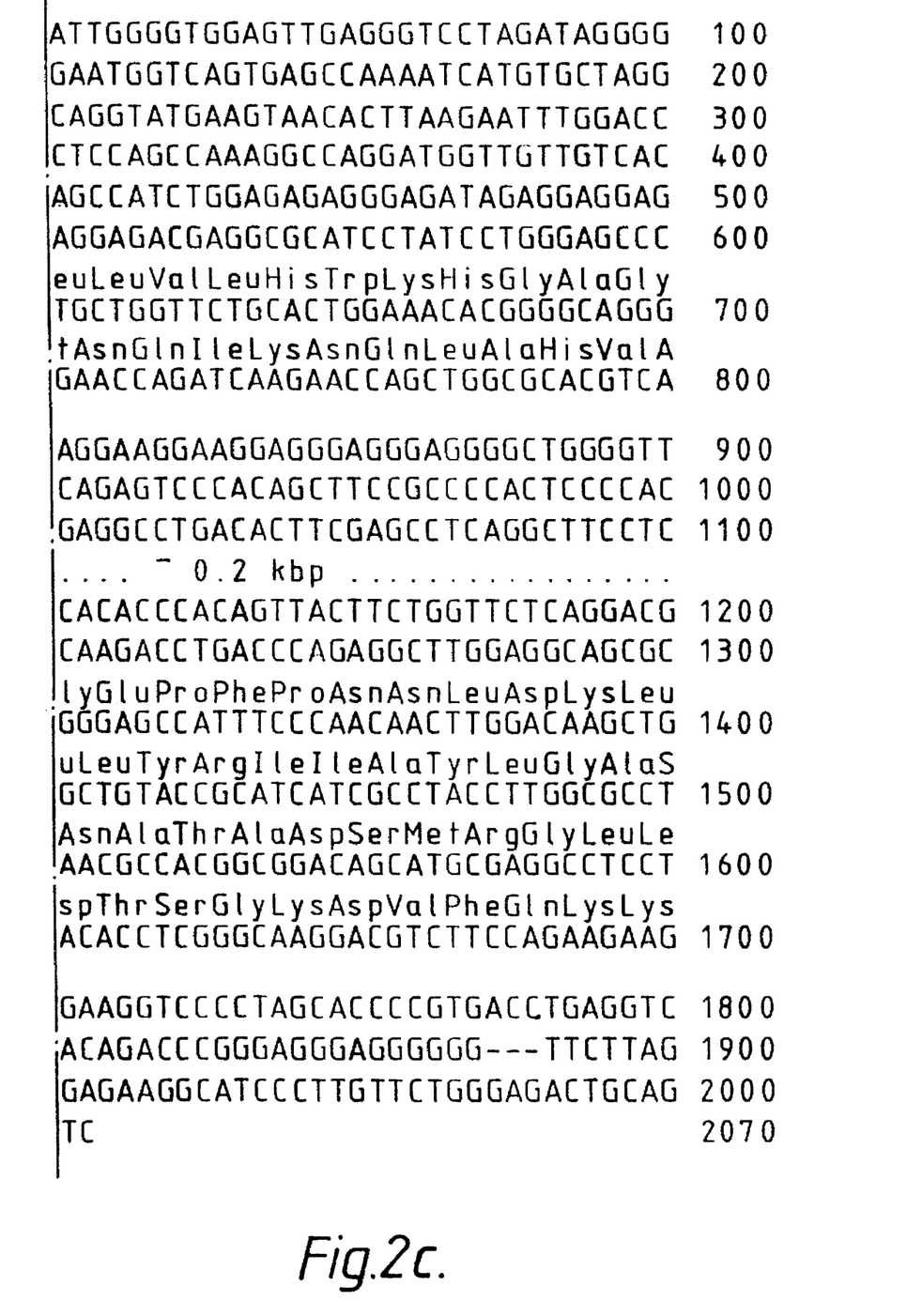
Figure 3:
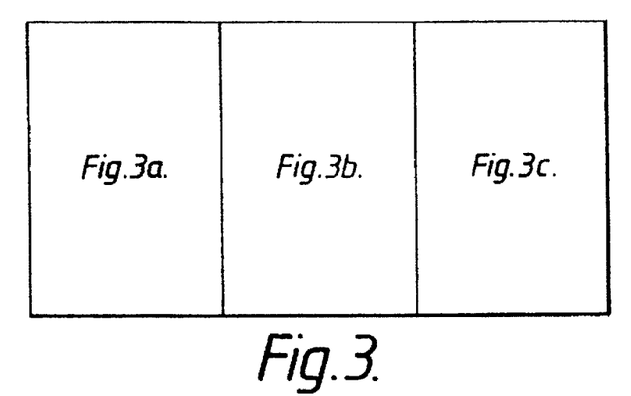
Figure 3A:
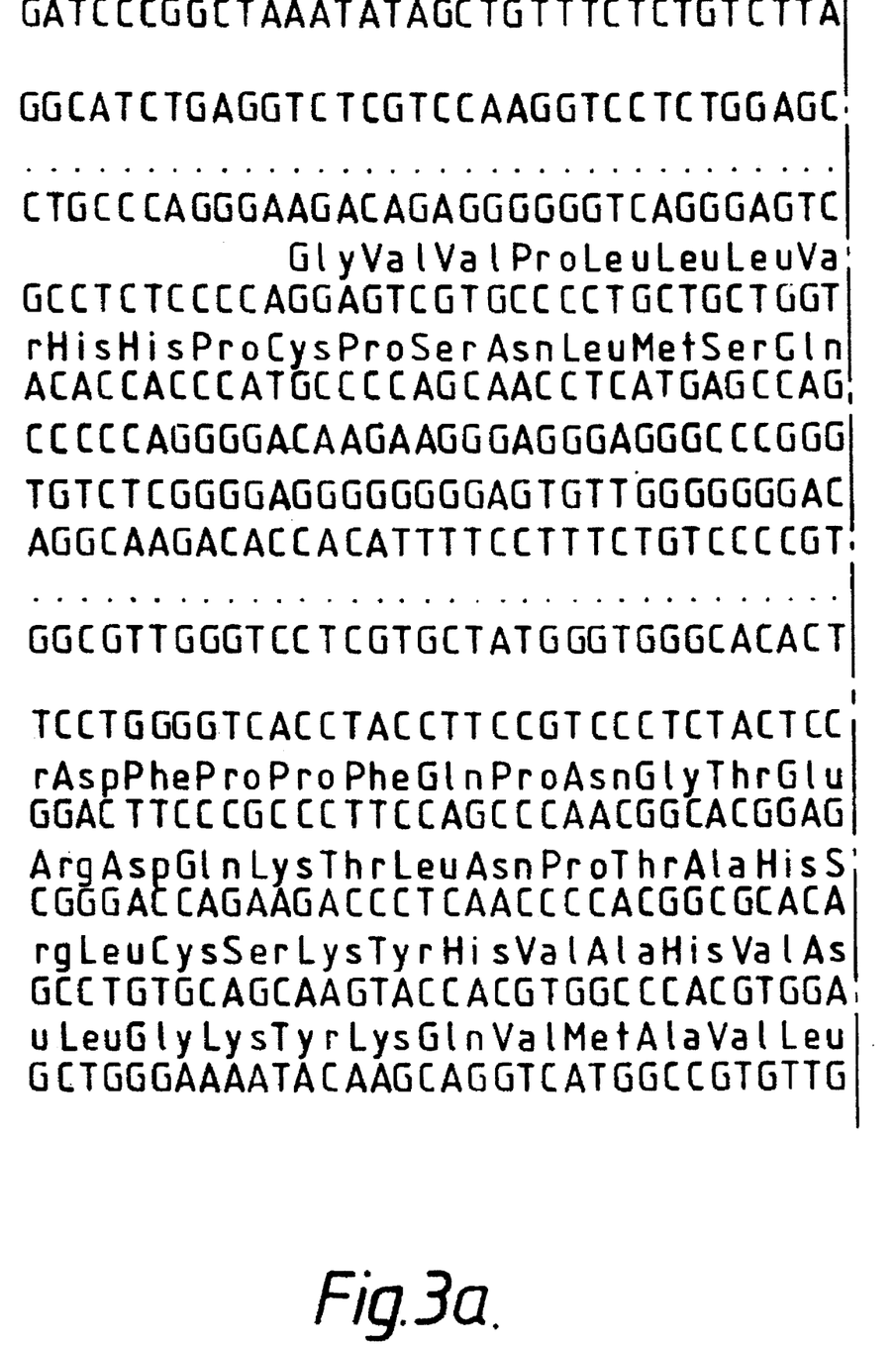
Figure 3B:
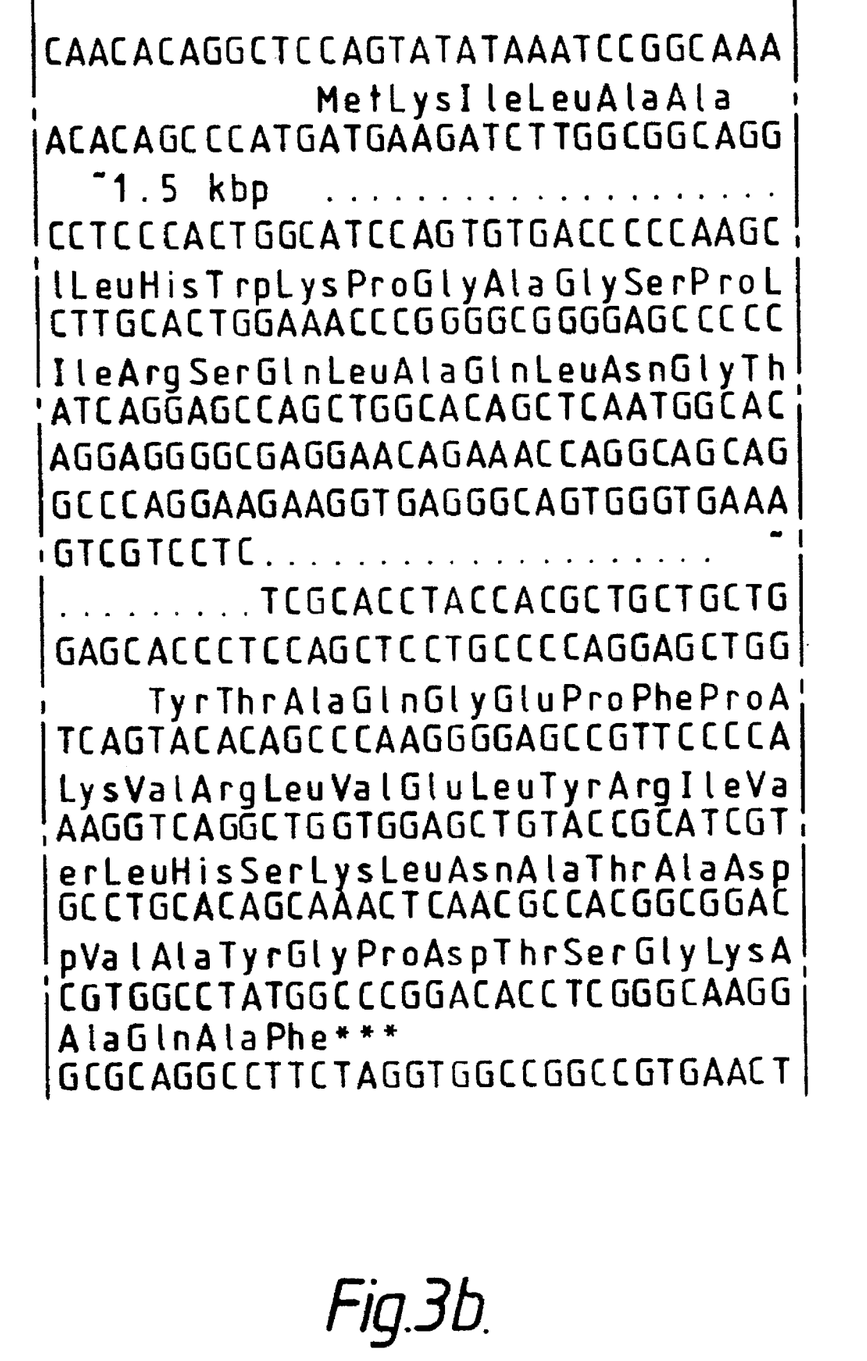
Figure 3C:
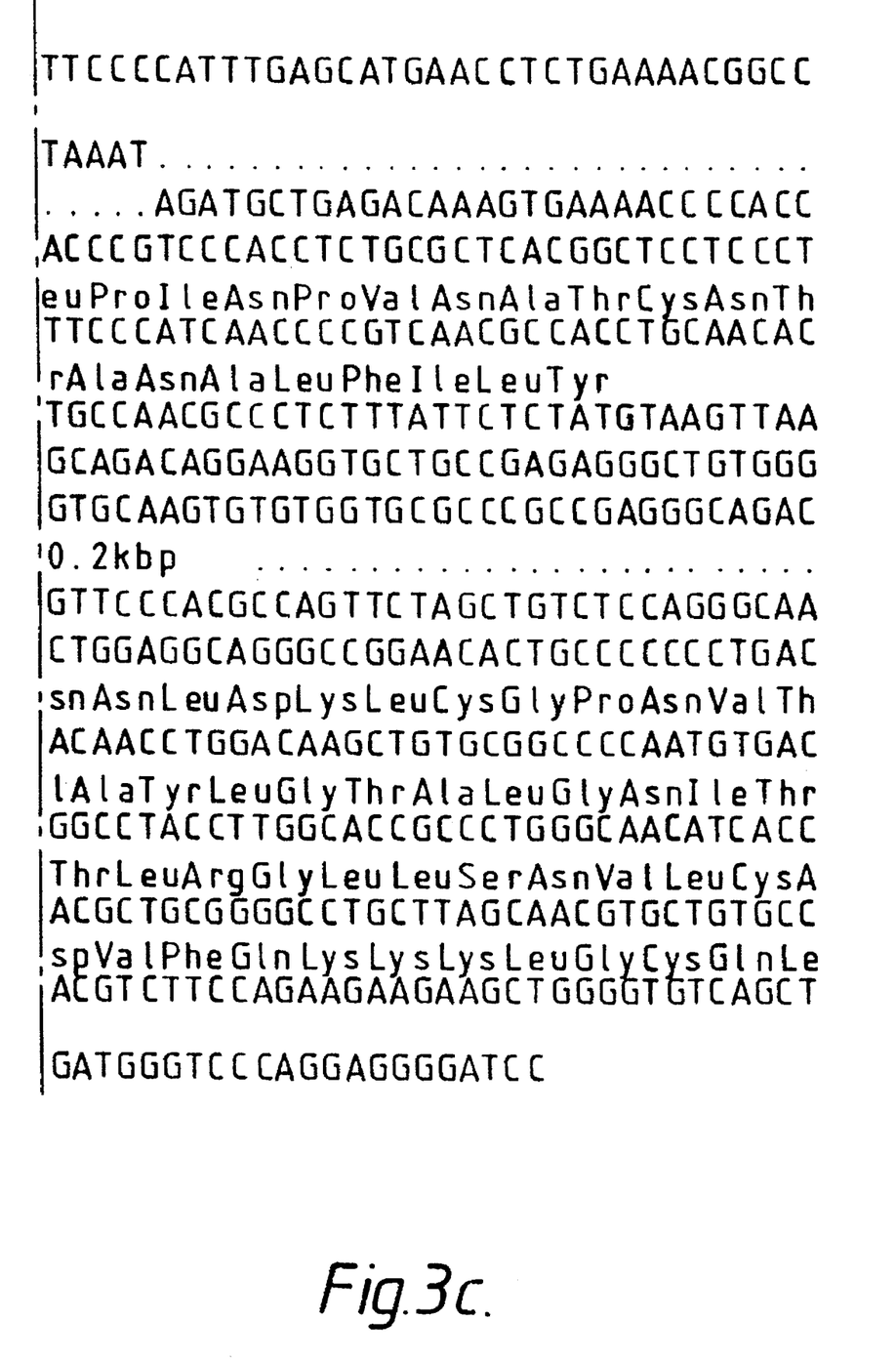
Figure 4:
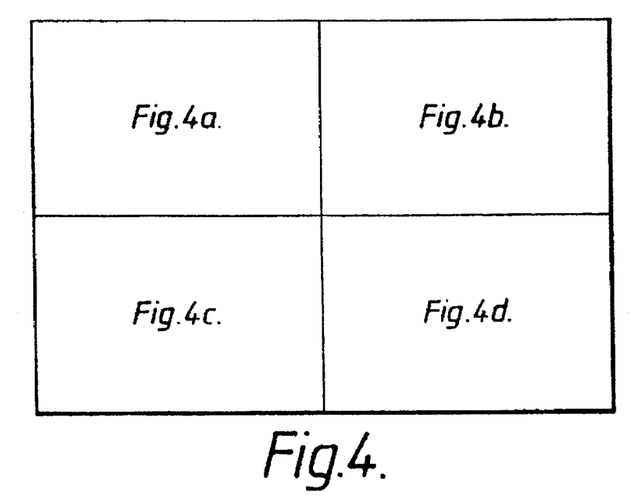
FIGS. 4a–4d shows the amino acid sequence of porcine LIF and comparison with murine, human and ovine LIF. The amino acid sequence of murine LIF (M) as determined by direct amino acid sequencing and nucleotide sequence analysis of LIF encoding cDNAs (PCT/AU88/00093) is listed on the top line, the corresponding human and ovine amino acid sequences (H and O) determined by nucleotide sequence analysis of the human and ovine LIF genes (PCT/AU88/00093) in the middle, and the corresponding sequence of porcine LIF (P) on the bottom line. The N-terminal residue of mature murine LIF, determined by direct amino acid sequencing, is designated +1. Identities between murine and human, between human and ovine or between ovine and porcine LIF are indicated by asterisks and conservative substitutions (Arg/Lys; Glu/Asp; Ser/Thr; Ile/Leu/Val) by dashes.
Figure 4A:
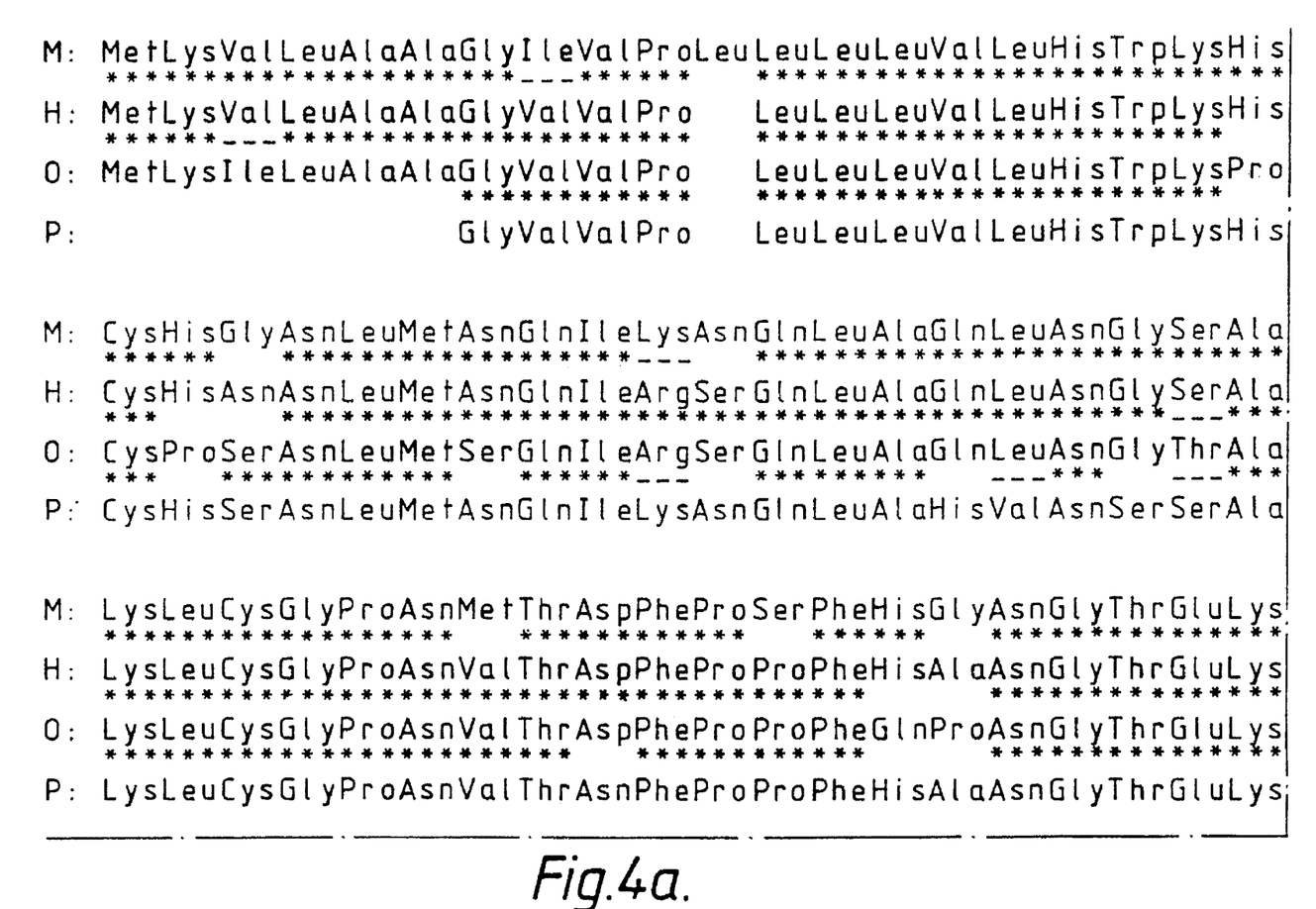
Figure 4B:
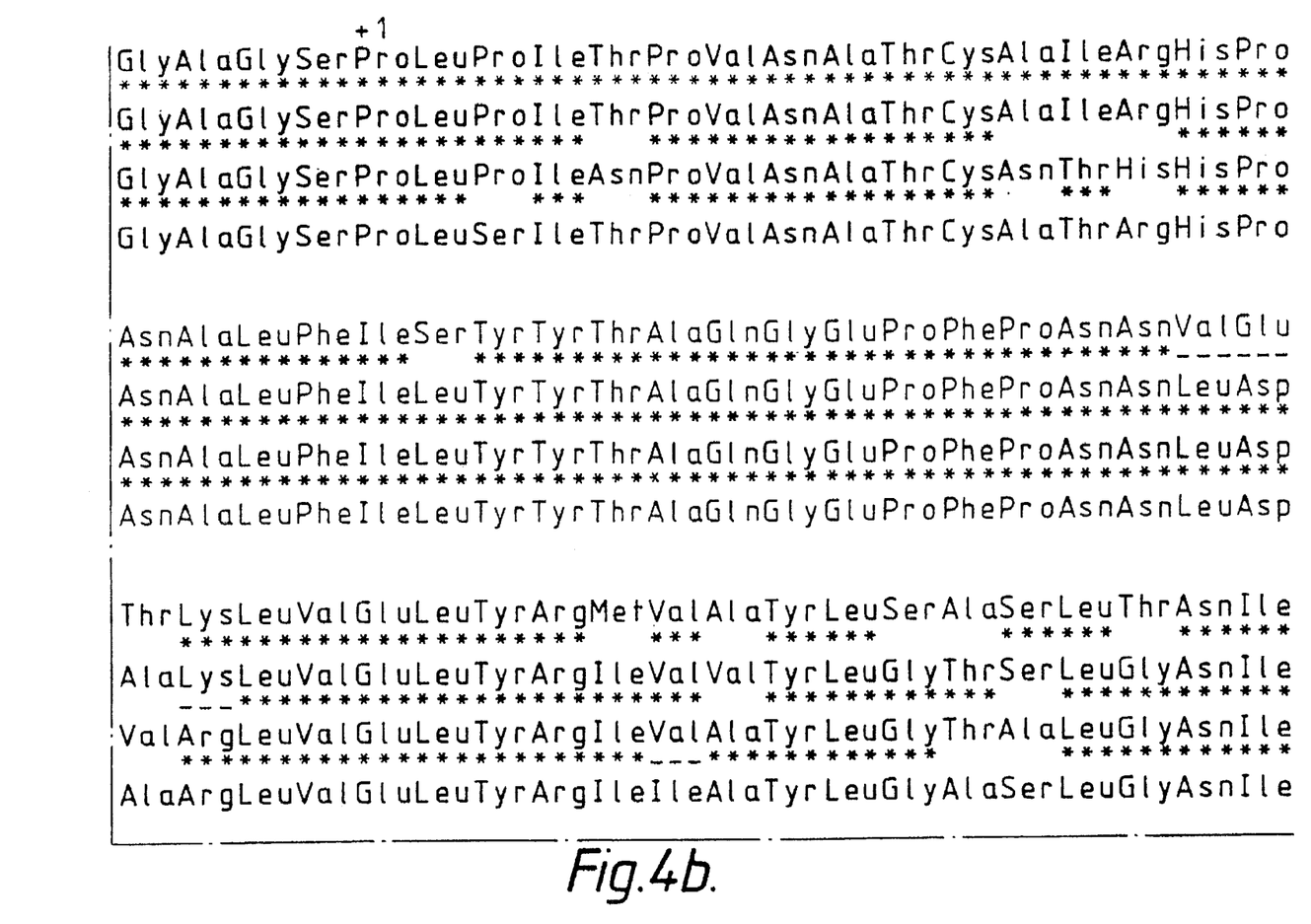
Figure 4C:
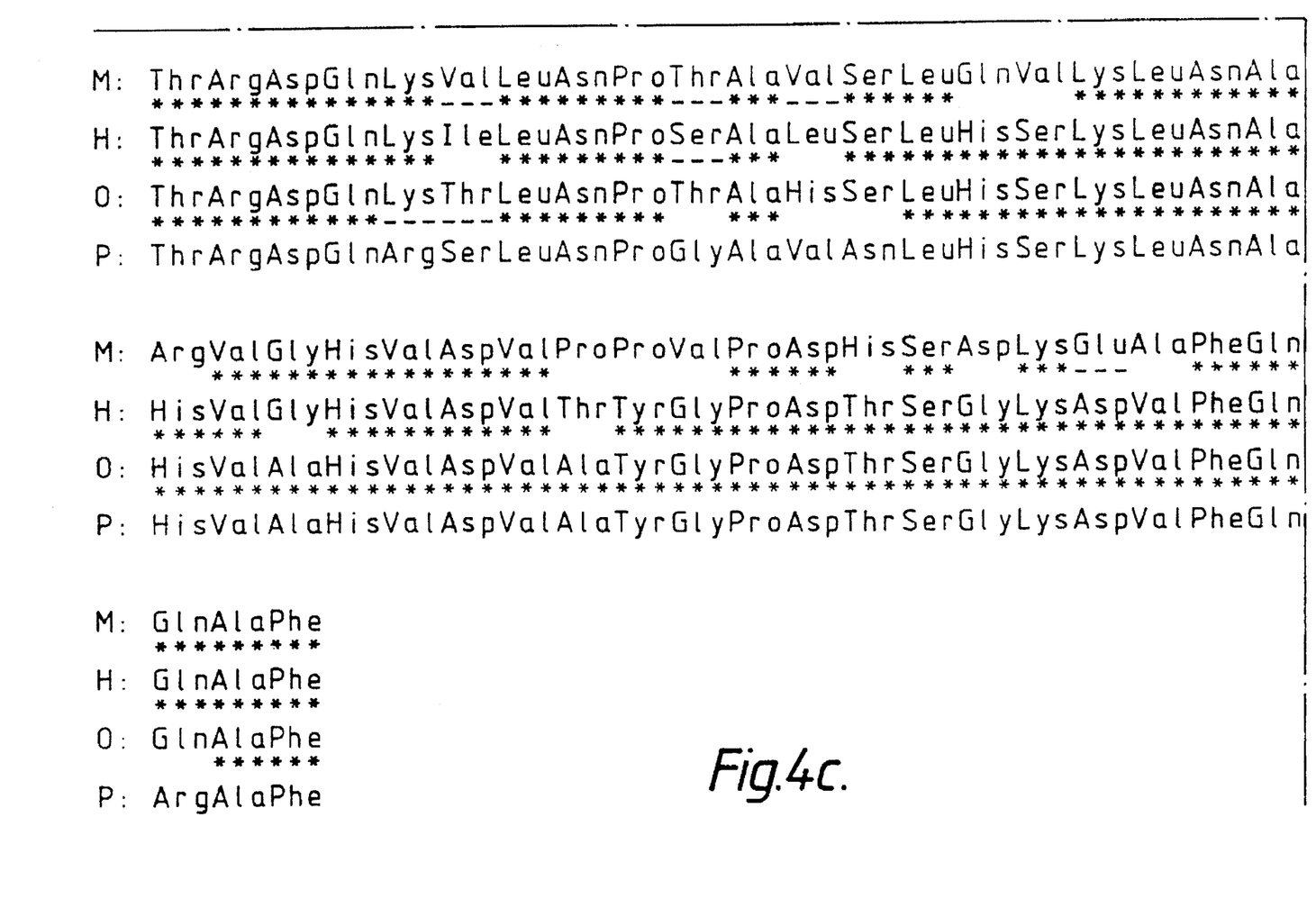
Figure 4D:
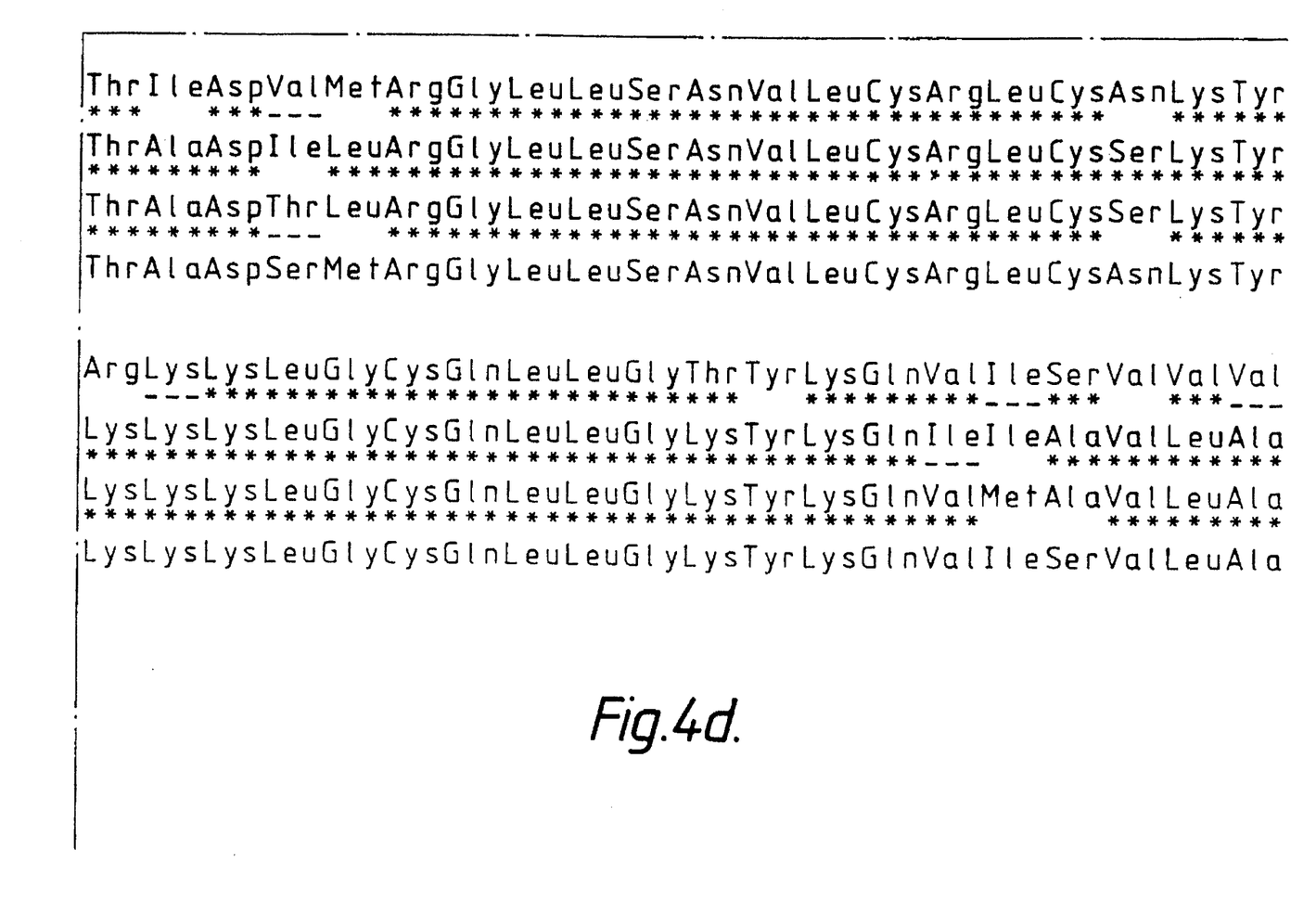

Identification of Mammalian LIF Genes by Cross-hybridization with a Murine LIF cDNA Probe A method has been previously disclosed (PCT/AU88/00093) for using a radioactively labelled fragment of mouse LIF cDNA as a hybridization probe to detect the human LIF gene on Southern blots. FIG. 1 demonstrates that similar conditions can be used to detect presumptive LIF gene homologues in a variety of mammalian DNAs, including sheep, pig, cow, guinea pig, dog, monkey, human and rat. Note that in each species, using this probe, only a unique gene is detected, with no evidence for reiterated sequences. Note also that the intensity of hybridization of the presumptive LIF gene homologues is less than that of the murine probe to rodent DNA, implying a lower degree of homology.

Each track on the gel contains 10 µg of genomic DNA from each of the indicated species, digested to completion with the restriction endonuclease BamHI. After electrophoresis through a 0.8% w/v agarose gel and transfer to nitrocellulose using standard conditions, the immobilized DNA was hybridized with a fragment of murine LIF cDNA from clone pLIF7-2b (PCT/AU88/00093) $^{32}$p-labelled by nick-translation to a specific activity of ~2–×10$^8$ cpm/µg. The filter was prehybridized and hybridized at 65° C. in 0.9M NaCl, 0.09M Sodium citrate (6×SSC), 0.2% w/v Ficoll, 0.2% w/v polyvinylpyrollidine, 0.2% w/v bovine serumalbimun, 50 µg/ml E.coli tRNA, 0.1 mM ATP and 2 mM sodium pyrophosphate. During hybridization, 0.1% w/v SDS was included and the probe was included at ~2×10$^7$ cpm/ml. After hybridization at 65° C. for 16 hours, the filter was extensively washed in 2×SSC, 0.1% w/v SDS at 65° C. and then autoradiographed using a Kodak XAR5 film and 2 screens at −70° C.

EXAMPLE 2

Isolation of the Porcine LIF Gene

A library of porcine genomic DNA, partially digested with Sau 3A, was screened for LIF gene-containing clones by hybridization with both a murine LIF cDNA and a portion of the human LIF gene as probes. The murine LIF cDNA fragment used as a probe corresponded to the LIF coding region and was derived from clone pLIFmutl; the human gene fragment used as a probe corresponded to the 3 kbp BamH1 fragment spanning the human LIF gene and was derived from clone pHGLIFBaml (PCT/AU88/00093). Conditions of hybridization were as previously disclosed (PCT/AU88/00093). Briefly, phage plaques representing the genomic library were grown at a density of 50,000 plaques per 10 cm petri dish and transferred to nitrocellulose as described in Maniatis etal. (1982). Four nitrocellulose filters were prepared from each dish. Prior to hybridization, filters were incubated for several hours at 65° C. in 6×SSC (SSC=0.15M NaCl, 0.015M sodium citrate), 0.2% w/v Ficoll; 0.2% w/v polyvinylpyrollidine; 0.2% w/v bovine serum albumin, 2 mM sodium pyrophosphate, 1 mM ATP, 50 µg/ml E. coli tRNA 0.1% w/v SDS at 65° C. for 16–18 hours. The murine LIF cDNA and human LIF genomic DNA fragments were each radioactively labelled by nick-translation using [α-$^{32}$P] dATP to a specific activity of ~2×10$^8$ cpm/µg or by random priming to a specific activity of ~10$^9$ cpm/µg and were included in the hybridization at a concentration of ~2×10$^6$ cpm/ml. For each petri dish, 2 nitrocellulose filters were hybridized with the murine probe and two with the human probe. After hybridization, filters were extensively washed in 6×SSC, 0.1% w/v SDS at 65° C. and then autoradiographed. Plaques positive on quadruplicate filters were picked and rescreened at lower density, as before. The use of two different probes simultaneously reduced the chance of identifying clones containing short sequence segments displaying fortuitous to one or other of the probes. Of the clones originally identified, one (λPGLIF-E2) was purified. DNA from this λ clone was digested with a series of restriction endonucleases (including SalI which liberates the entire segment of cloned genomic DNA). After digestion of the recombinant phage DNAs and resolution by electrophoresis on agarose gels, the DNA was transferred to nitrocellulose and hybridized with the mouse LIF cDNA probe (under the conditions outlined above) to reveal the fragments containing the LIF gene. Even after washes of higher stringency (0.2×SSC, 65° C.) the porcine DNA still displayed strong hybridization with the murine probe. A 2.4 kbp BamHI fragment hybridizing to the murine cDNA probe and corresponding in size to that identified in Southern blots of porcine genomic DNA was identified and subcloned into the plasmid vector pUC12, giving rise to clone pPLIFBaml.

EXAMPLE 3

Isolation of the Ovine LIF Gene

A library of ovine genomic DNA, partially digested with Sau 3A and ligated with the lambda phage cloning vector EMBL 3A, was screened for LIF gene-containing clones by hybridization with both a murine LIF cDNA and a portion of the human LIF gene as probes. The murine LIF cDNA fragment used as a probe corresponded to the 3 kbp BAMHI fragment spanning the human LIF gene and was derived from clone pHGLIFBaml (PCT/AU88/00093). Conditions of hybridization were as disclosed in PCT/AU88/00093 and Example 2.

Of the 8 clones originally identified, one (λOGLIFR2) was purified. DNA from this λ clone was digested with a series of restriction endonucleases (including SalI which liberates the entire segment of cloned genomic DNA). After digestion of the recombinant phage DNAs and resolution by electrophoresis on agarose gels, the DNA was transferred to nitrocellulose and hybridized with the mouse LIF cDNA probe (under the conditions outlined above) to reveal the fragments containing the LIF gene. Even after washes of higher stringency (0.2×SSC, 65° C.) the ovine DNA still displayed strong hybridization with the murine probe. A ~3 kbp BamHI fragment hybridizing to the murine cDNA probe was identified and subcloned into the plasmid vector pEMBL8+, giving rise to clone pOGLIFBaml.

EXAMPLE 4

Determination of Nucleotide and Amino Acid Sequences of the Porcine and Ovine LIF Nucleotide sequencing was performed by the dideoxy chain termination method (Sanger et al, 1977) using the SEQUENASE (registered trade mark) reagents and protocol (United States Biochemicals). The nucleotide sequences of porcine and ovine LIF DNA are shown in FIGS. 2 and 3. Templates were single-stranded DNA of various fragments derived from the 2.4 kbp BamHI fragment of pPLIFBaml or the 3 kbp BamHI fragment of pOGLIFBaml subcloned into M13 phage vectors (Messing and Vieira 1982). The primers used were both an external primer in the M13 sequence and a variety of oligonucleotides complementary to sequences within the gene.

The porcine and ovine LIF sequences thus determined are shown in FIGS. 2 and 3, respectively. Alignment of these sequences with the human and mouse gene sequences reveal that they contain coding regions specifying proteins highly homologous to murine and human LIF. The protein sequence encoded by these coding regions are listed above the nucleotide sequences.

The complete amino acid sequence of porcine and ovine LIF are aligned with the murine and human LIF sequences in FIG. 4 with identities indicated by asterisks and conservative substitutions by dashes. Many large blocks of amino acid sequence remain totally conserved between all four species. However, it is evident that the porcine sequence is more closely related to the ovine than the human and murine sequence. A comparison of each of these four LIF sequences is presented in Table 1, in which only the mature portion of the LIF molecule is considered, excluding the hydrophobic leader. Only identities are scored in this comparison.

TABLE 1

| Comparison of LIF amino acid sequences (Percent Identity) | | | | |
|---|---|---|---|---|
| | MURINE | HUMAN | OVINE | PORCINE |
| MURINE: | 100 | 78 | 74 | 77 |
| HUMAN: | | 100 | 88 | 85 |
| OVINE: | | | 100 | 83 |
| PORCINE: | | | | 100 |

The methods disclosed in PCT/AU88/00093 can be used for the construction of a variety of expression vectors carrying the livestock (eg ovine or porcine) LIF gene. Such vectors include yeast (e.g. YEpsecl, Baldari et. al, 1987), and E.coli e.g., vector pGEX-2T, Smith and Johnson, 1988 Gearing etal. 1989;). Conditions for expression are as disclosed in PCT/AU88/00093.

EXAMPLE 5

The enhancement of the development of 8 cell murine embryos by addition of LIF is described in the following example, which is included by way of illustration and not limitation of the present invention.

1. Materials and Methods

Animals

Balb-C×C57 three to four weeks old F1 female mice were primed with 7.5 iu PMSG (Folligon; Intervet, Australia) followed 48 hours later, with 7.5 iu hCG (Chorulon; Intervet, Australia) to achieve superovulation. Immediately following the hCG (Human chorionic Gonadotrophin) injection, treated females were placed with fertile males (CBA C57 strain, one female plus one male per cage). The next morning each female was checked for the presence of a vaginal plug as evidence of mating. This was then considered as Day 1 of pregnancy.

Media

The culture medium was prepared from powdered Minimal Essential Medium (MEM; Eagle, with Earle's salts, with L-glutamine without sodium bicarbonate; Flow Laboratories, UK) dissolved in Milli-Q water and supplemented with 1 μg/ml glucose, 25 mM sodium bicarbonate and 10% (v/v) heat-inactivated fetal calf serum (FCS; CSL, Australia). An antibiotic/antimycotic solution was also added to provide per 100 ml of solution, 10,000 units penicillin, 10,000 μg streptomycin and 25 μg fungizone (CSL, Australia). The pH and osmolarity of the media were adjusted to 7.40 and 280 mOsm respectively. At this point the media was sterilised by filtration (Acrodisc 0.2 um filter; Gelman Sciences Inc., USA).

Embryos

On Day 3 of pregnancy females were killed between 1300–1500 hours, i.e. 71–73 hours post-hCG injection, by cervical dislocation. The whole reproductive tract was dissected out and placed in Earle's Balanced Salt Solution without Calcium and Magnesium (EBS9) at 37° C. Subsequently, 8-cell embryos were teased/flushed out of the oviduct-uterus junction and after washing once in culture medium were placed into control or experimental group (see below) and maintained in a humidified gas environment of 5% $CO_2$ in air, at 37° C.

Culture of Embryos

For experimentation, 8-cell embryos were randomly assigned to a control or experimental group with each group consisting of eight replicates with embryos from four to six mice used per replicate. Embryos were added 10–20 per well approximately 15–20 minutes after recovery from the uterus and maintained in vitro for a period of five days in wells containing the culture media alone (1 ml/well) or the culture media with LIF (1000 u/ml) supplementation as indicated. This dosage of LIF was chosen as it is optimal for the inhibition of differentiation of ES cells (International Patent Application No. PCT/AU89/00330).

Assessment of Morphological Development

Observations on embryo development were made daily using an inverted microscope and the numbers of embryos achieving morula, blastocyst or hatching blastocyst stage recorded (Hsu, 1979). On Days 4–5 of culture, many embryos underwent developmental changes associated with implantation (Sherman, 1978). For this study, post hatching embryos were recorded as achieving stage 1 when they displayed proliferating trophectoderm cells, and stage 2 when they showed outgrowth of trophectoderm cells.

2. Results

The effect on the development of the mouse 8-cell embryos in vitro of including LIF ($10^3$ units/ml in culture medium, prior, to (PRE) or following (POST) formation of the blastocysts are shown in Table 2. The results are expressed as % initial number of embryos (n=35) completing the developmental stage.

TABLE 2

| LIF | | | |
|---|---|---|---|
| PRE | POST | 8-cell → BLASTOCYST | → IMPLANTATION |
| *– | – | 100 | 57.6 |
| + | – | 100 | 67.2 |
| – | + | 100 | 85.7 |
| + | + | 99 | 77.2 |

Control only

By combining data on all experiments where LIF ($10^3$ units/ml) has been added to the culture medium, a definite effect has been found where the addition of LIF enhances the development of 8 cell mouse embryos to the implantation stage 2 (see Materials and Methods—Assessment of Morphological Development) as follows:

| | Control | LIF |
|---|---|---|
| Embryos to Implantation Stage 2 = | 226 | 156 |
| Total No. 8-cell Embryos Cultured | 349 | 195 |
| | (64%) | (80%) |

($x^2 = 27.0$ P ≦ 0.001)

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

EXAMPLE 6

Expression of Ovine LIF

A contiguous coding region for ovine LIF was constructed by intron removal and site directed mutagenesis in a manner analogous to the human LIF gene as previously described.

The ovine LIF coding region so constructed was cloned into yeast expression vector YEpsec-1 in the correct (clones 3 and 15) and incorrect (clone 5) orientation. LIF activity was determined and the results are shown in Table 3. LIF activity is expressed as Units/ml as determined using the M1 cell differentiation bioassay as described before. The mouse positive control (mouse +ve) is a yeast clone containing YEpsec-1 with the murine LIF gene inserted in the correct orientation.

TABLE 3

| Yeast Clone | LIF Activity (Units) (Units/ml) |
|---|---|
| Clone 3 | 10,700 |
| Clone 15 | 829,000 |
| Clone 5 | 0 |
| mouse +ve | 61,400 |

EXAMPLE 7

Receptor Binding Competition Assay

The receptor binding competition assay was performed as previously described. The assay shows the ability of yeast derived sheep LIF to compete with iodinated murine LIF for binding to specific cellular receptors on mouse liver cells.

TABLE 4

| Competitor | [ ](ng/ml) | $^{125}$I.LIF Specifically bound cpm |
|---|---|---|
| pure rec. human (E. coli) | 10000 | 0 |
| | 1000 | 323 |
| | 100 | 575 |
| | 10 | 258 |
| | 1 | 1053 |
| | 0.1 | 1279 |
| | 0.01 | 1600 |
| pure rec human LIF (yeast) | 100 | 614 |
| | 1 | 1078 |
| crude sheep LIF (yeast) | 1:1 | 625 |
| | 1:10 | 822 |
| Saline | — | 2549 |
| untransf. yeast medium | 1:1 | 2603 |
| | 1:10 | 2591 |

REFERENCES CITED

Baldari et al. *EMBO J* 6: 229–234, 1987

Hsu Y-C, *Developmental Biology* 68 4530616, 1979

Maniatis et al. *Molecular Cloning. A Laboratory Manual.* Cold Spring Harbor Laboratory, Cold Spring Harbor USA 1982

Messing and Vieira, *Gene* 19: 269–276, 1982

Sanger et al. *Proc. Natl. Acad. Sci. USA* 74: 5463–5462, 1977

Sherman, *Methods in Mammalian Reproduction*, New York: Academic Press pp 81–125, 1978

Smith and Johnson *Gene* 67: 31–40, 1988

Gearing, Nicola, Metcalf, Foote, Willson, Gough and Williams *Biotechnology:* 1157–1161, 1989

We claim:

1. A method for the in vitro development of a mammalian embryo to the implantation stage which method comprises culturing the embryo in vitro in a culture medium comprising an effective amount of mammalian LIF for a time and under conditions sufficient to develop an embryo to implantation stage.

2. The method according to claim 1 wherein the mammalian embryo is of human, murine or livestock animal origin.

3. The method according to claim 2 wherein the mammalian embryo is isolated from a livestock species.

4. The method according to claim 3 wherein the mammalian LIF is from human, mouse or livestock species.

5. The method according to claim 4 wherein the mammalian LIF is from livestock species.

6. The method according to claim 5 wherein the livestock species is a sheep, pig, goat, cow, horse or donkey.

7. The method according to claim 6 wherein the livestock species is a sheep or a pig.

* * * * *